US00PP14474P39

(12) United States Plant Patent
Pieters

(10) Patent No.: US PP14,474 P3
(45) Date of Patent: Jan. 20, 2004

(54) CHRYSANTHEMUM PLANT NAMED 'GEDI TWO CAN'

(50) Latin Name: *Chrysanthemum morifolium*
Varietal Denomination: Gedi Two Can

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 10/137,818

(22) Filed: May 1, 2002

(65) Prior Publication Data

US 2003/0208816 P1 Nov. 6, 2003

(51) Int. Cl.[7] ..... A01H 5/00
(52) U.S. Cl. ..... Plt./291

(58) Field of Search ..... Plt./291, 287, 292

(56) References Cited

U.S. PATENT DOCUMENTS

PP10,215 P 1/1998 Pieters ..... Plt./289
PP11,300 P 3/2000 Boeder ..... Plt./287

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar is disclosed, characterized by a decorative-type inflorescence, consistent flowering response to short days, blooming consistently after 49 days of short day length, free branching habit, purple ray florets, a very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Gedi Two Can.'

BACKGROUND OF THE INVENTION

The new cultivar is a product of hybridization of a female parent Chrysanthemum plant variety 'Paularo Lilac' (undistributed in the United States) and a male parent Chrysanthemum plant variety 'Dark Veria' (U.S. Plant Pat. No. 10,215). The new cultivar was discovered and selected by the inventor in October 1997.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Gedi Two Can' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Can.' These characteristics in combination distinguish 'Gedi Two Can' as a new and distinct Chrysanthemum cultivar:

1. Decorative-type inflorescence,
2. Consistent flowering response to short days, blooming consistently after 49 days of short day length,
3. Free branching habit, 4. Purple ray florets,
5. Very uniform round growth habit, and
6. Large quantity of blooms per flowering branch.

Plants of the new cultivar are similar to plants of the female parent variety, 'Paularo Lilac' in most horticultural characteristics, however plants of the new cultivar have differently colored ray florets than plants of the female parent variety.

Plants of the new cultivar are similar to plants of the male parent variety, 'Dark Veria' in most horticultural characteristics, however plants of the new cultivar have differently colored ray florets and the plants naturally bloom earlier than plants of the male parent variety.

In comparison to the commercially available variety 'Cleargar VZP1' (U.S. Plant Pat. No. 11,300), 'Gedi Two Can' naturally blooms earlier and inflorescences of a smaller diameter, more inflorescences per flowering branch, and lighter colored ray florets.

BRIEF DESCRIPTION OF THE PHOTOGRAPHS

The photograph shows a plant of 'Gedi Two Can' grown in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in Oxnard, Calif. during the month of December and January. The age of the observed plants is 79 days from a rooted cutting. The growing temperature ranged from 55° to 68° F. at night to 60° to 75° F. during the day. Measurements and numerical values represent averages of typical flowering types.

Botanical classification: *Chrysanthemum morifolium* cultivar 'Gedi Two Can'.
Commercial classification: Garden-type Chrysanthemum.
Parentage: Hybridization of a female parent Chrysanthemum plant variety, 'Paularo Lilac' (undistributed in the United States), and a male parent Chrysanthemum plant variety 'Dark Veria' (U.S. Plant Pat. No. 10,215).

PROPAGATION

Time to rooting: 7 to 14 days at approximately 21° C.
Root description: Fine, fibrous.

PLANT

Growth habit: Mounding herbaceous perennial.
Height: Approximately 17.3 cm.
Spread: Approximately 22 cm.
Growth rate: Moderate.
Branching characteristics: Free Branching.
Length of lateral branches: Approximately 19 cm.
Number of leaves per lateral branch: Approximately 12.

FOLIAGE

Leaf:
- *Arrangement.*—Alternate.
- *Average length.*—Approximately 6.1 cm.
- *Average width.*—Approximately 5.9 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near 137A. Young foliage under side: Near 138B. Mature foliage upper side: Near 137A. Mature foliage under side: Near 138B. Venation upper side: Near 145B. Venation under side: Near 138C.
- *Venation type.*—Palmately net.

Petiole:
- *Average length.*—Approximately 2.4 cm.
- *Color.*—Near 137A.
- *Diameter.*—Approximately 0.3 cm.

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the middle two weeks of September.
- *Number of inflorescences per lateral branch.*—Approximately 16.
- *Inflorescence diameter.*—Approximately 3.8 cm.
- *Inflorescence depth.*—Approximately 1.5 cm.
- *Inflorescence longevity on plant.*—Approximately 30 days.
- *Persistence.*—Persistent.

Ray florets:
- *Appearance.*—Matte.
- *Texture.*—Smooth.
- *Average number per flower.*—163.
- *Shape.*—Spatulate.
- *Aspect.*—Flat.
- *Margin.*—Entire.
- *Apex.*—Retuse.
- *Length.*—Approximately 1.7 cm.
- *Width.*—Approximately 0.6 cm.
- *Color.*—Upper surface at first opening: Near 75A. Upper surface at maturity: Near 75B. Upper surface at fading: Near 75C. Under surface at first opening: Near 75A. Under surface at maturity: Near 75A. Under surface at fading: Near 75C with near 75A around upper outer edge.

Disc florets:
- *Appearance.*—Shiny.
- *Texture.*—Smooth.
- *Average number per flower.*—Approximately 10.
- *Shape.*—Cylindrical.
- *Apex.*—Obtuse.
- *Average length.*—Approximately 0.5 cm.
- *Average width.*—Approximately 0.1 cm.
- *Color.*—At first opening: Near 154A. At maturity: Near 13B. At fading: Near 13A.

Peduncle:
- *Length.*—At terminal end (shortest): Approximately 4.2 cm. At lateral end (longest): Approximately 7 cm.
- *Angle to stem.*—Acute.
- *Strength.*—Moderate.
- *Color.*—Near 143C.
- *Habit.*—Upright.
- *Diameter.*—Approximately 0.2 cm.
- *Surface texture.*—Lightly pubescent.

Inflorescence bud:
- *Length.*—Approximately 0.7 cm.
- *Diameter.*—Approximately 0.8 cm.
- *Form.*—Globular.
- *Color.*—Near 1C.

Involucral bracts (phyllaries):
- *Appearance.*—Matte.
- *Texture.*—Lightly pubescent.
- *Number.*—Approximately 90 throughout entire inflorescence.
- *Shape.*—Oblanceolate.
- *Margin.*—Entire.
- *Apex.*—Acute.
- *Length.*—Approximately 0.7 cm.
- *Width.*—Approximately 0.2 cm.
- *Color.*—Upper side: Near 144A. Under side: Near 144A.

REPRODUCTIVE ORGANS

Ray florets:
- *Number of pistils per flower.*—1.
- *Stigma shape.*—2 branched.
- *Stigma color.*—Near 9A.
- *Style color.*—Near 154D.
- *Style length.*—Approximately 0.5 cm.
- *Stamens.*—Absent.

Disc florets (hermaphroditic):
- *Number of pistils per flower.*—1.
- *Stigma shape.*—Two-branched.
- *Stigma color.*—Near 13A.
- *Style length.*—Approximately 0.4 cm.
- *Style color.*—Near 154C.
- *Number of stamens per flower.*—5.
- *Anther shape.*—Tubular.
- *Anther color.*—Near 15A.
- *Pollen color.*—Near 15A.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests has been observed in this cultivar.

Heat and cold resistance: Plants with flowers are hardy to low temperatures about −2° C. Non flowering plants are hardy in the approximate range of 3° C. to −6° C., depending upon duration of cold and amount of moisture in the soil. With adequate water plants are hardy to a high temperature of 49° C.

What is claimed is:

1. A new and distinct cultivar of Chrysanthemum plant named 'Gedi Two Can' as herein illustrated and described.

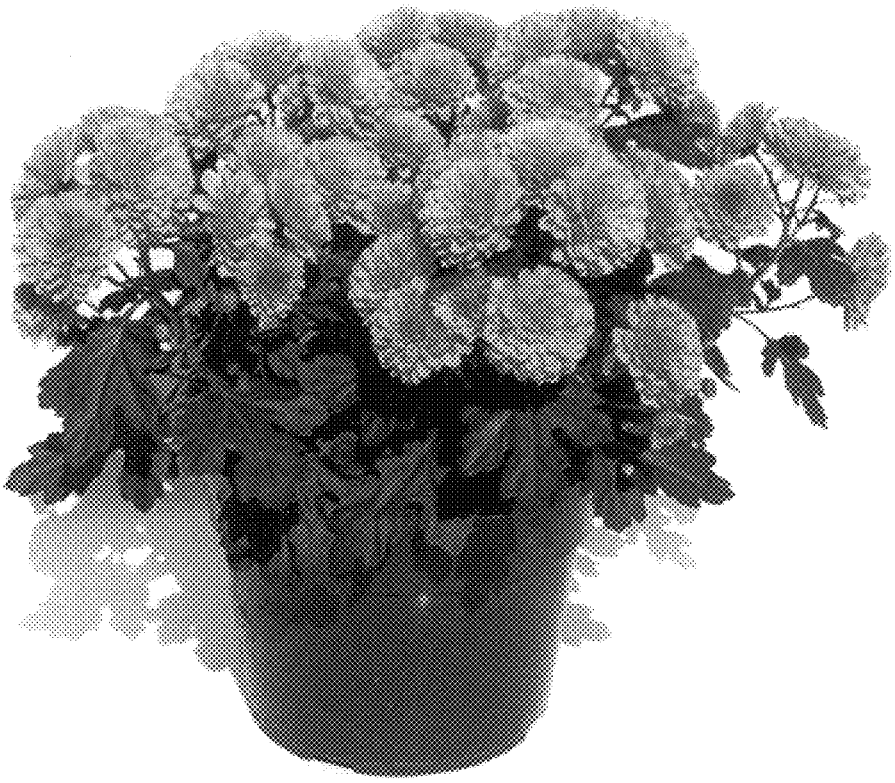

* * * * *